United States Patent
Morris et al.

(10) Patent No.: US 11,851,420 B2
(45) Date of Patent: *Dec. 26, 2023

(54) PYRAZOLE DERIVATIVES

(71) Applicant: SYNGENTA CROP PROTECTION AG, Basel (CH)

(72) Inventors: James Alan Morris, Bracknell (GB); Sally Elizabeth Russell, Bracknell (GB); Sean Ng, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,744

(22) Filed: Dec. 7, 2022

(65) Prior Publication Data

US 2023/0114845 A1 Apr. 13, 2023

Related U.S. Application Data

(63) Continuation of application No. 17/108,110, filed on Dec. 1, 2020, now Pat. No. 11,548,873, which is a continuation of application No. 16/782,866, filed on Feb. 5, 2020, now Pat. No. 10,882,846.

(30) Foreign Application Priority Data

Feb. 5, 2019 (GB) ..................... 1901559

(51) Int. Cl.
| | |
|---|---|
| *C07D 403/04* | (2006.01) |
| *A01N 43/54* | (2006.01) |
| *A01N 43/58* | (2006.01) |
| *A01N 43/80* | (2006.01) |
| *A01N 43/90* | (2006.01) |
| *C07D 401/04* | (2006.01) |
| *C07D 401/14* | (2006.01) |
| *C07D 409/14* | (2006.01) |
| *C07D 413/04* | (2006.01) |
| *C07D 471/04* | (2006.01) |
| *C07D 487/04* | (2006.01) |
| *A01N 43/56* | (2006.01) |
| *C07D 207/337* | (2006.01) |
| *C07D 207/34* | (2006.01) |
| *C07D 207/325* | (2006.01) |

(52) U.S. Cl.
CPC ........... *C07D 403/04* (2013.01); *A01N 43/54* (2013.01); *A01N 43/56* (2013.01); *A01N 43/58* (2013.01); *A01N 43/80* (2013.01); *A01N 43/90* (2013.01); *C07D 207/325* (2013.01); *C07D 207/337* (2013.01); *C07D 207/34* (2013.01); *C07D 401/04* (2013.01); *C07D 401/14* (2013.01); *C07D 409/14* (2013.01); *C07D 413/04* (2013.01); *C07D 471/04* (2013.01); *C07D 487/04* (2013.01)

(58) Field of Classification Search
CPC .............. C07D 403/04; C07D 207/325; C07D 207/337; C07D 207/34; C07D 401/04; C07D 401/14; C07D 409/14; C07D 413/04; C07D 471/04; C07D 487/04; A01N 43/54; A01N 43/56; A01N 43/58; A01N 43/80; A01N 43/90
USPC ...................................... 548/364.1
See application file for complete search history.

(56) References Cited

U.S. PATENT DOCUMENTS

| | | | |
|---|---|---|---|
| 5,763,470 | A | 6/1998 | Tang et al. |
| 9,365,522 | B2 | 6/2016 | Beck et al. |
| 10,294,202 | B2 | 5/2019 | Satterfield et al. |
| 10,851,085 | B2 * | 12/2020 | Morris .................... A01N 43/54 |
| 10,865,197 | B2 | 12/2020 | Morris et al. |
| 10,882,846 | B2 | 1/2021 | Morris et al. |
| 10,947,219 | B2 | 3/2021 | Morris et al. |
| 11,045,457 | B2 | 6/2021 | Cheruvallath et al. |
| 11,548,873 | B2 * | 1/2023 | Morris ................. C07D 207/34 |
| 2006/0127396 | A1 | 6/2006 | Ito et al. |
| 2007/0123508 | A1 | 5/2007 | Olsson et al. |

(Continued)

FOREIGN PATENT DOCUMENTS

| | | |
|---|---|---|
| EA | 202092054 A1 | 1/2021 |
| RU | 2658827 C2 | 6/2018 |
| WO | 2006/127396 A1 | 11/2006 |

(Continued)

OTHER PUBLICATIONS

International Search Report and Written Opinion for International Application No. PCT/EP2020/052780 dated Mar. 30, 2020.

(Continued)

*Primary Examiner* — Kristin A Vajda
(74) *Attorney, Agent, or Firm* — BakerHostetler; Toni-Junell Herbert

(57) ABSTRACT

The present invention relates to nitro-vinyl-pyrazole compounds of formula (B)

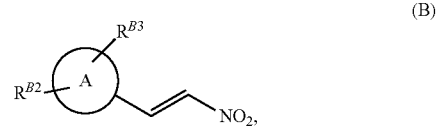

wherein ring A, $R^{B2}$ and $R^{B3}$ are as defined in claim 1, as well as the manufacture of such compounds and their subsequent use in the production of agrochemicals and/or pharmaceuticals.

21 Claims, No Drawings

(56) References Cited

U.S. PATENT DOCUMENTS

2019/0169153 A1  6/2019  Dugar et al.
2020/0061041 A1  2/2020  Cheruvallath et al.

FOREIGN PATENT DOCUMENTS

WO  2015084796 A1  6/2015
WO  2018065311 A1  4/2018

OTHER PUBLICATIONS

U.S. Appl. No. 16/782,530, filed Feb. 5, 2020 (Russell et al.).
U.S. Appl. No. 16/874,715, filed May 15, 2020 (Morris et al.).
U.S. Appl. No. 16/874,136, filed May 14, 2020 (Morris et al.).
U.S. Appl. No. 16/874,165, filed May 14, 2020 (Morris et al.).
U.S. Appl. No. 16/782,796, filed Feb. 5, 2020 (Russell et al.).
PGR2020-00028 Decision Granting Institution of Post-Grant Review; *Syngenta Crop Protection AG v. FMC Corporation*, dated Sep. 15, 2020.
Barnes, David M et al.: "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram" in JAGS Articles, 2002.
Evans, David A. et al.; "Ni(II)-Bis[(R, R)N, N-dibenzylcyclohexane-1,2-diamine]Br2 Catalyzed Enantioselective Michael Additions of 1,3-Dicarbonyl Compounds to Conjugated Nitroalkenes" in JAGS Communications, Jun. 23, 2005 (online).
Smit, et al., "Organic Synthesis: The Science Behind the Art", Journal of Chemical Education, 1 page (314), vol. 77, No. 3, Mar. 2020.

\* cited by examiner

PYRAZOLE DERIVATIVES

CROSS-REFERENCE TO RELATED APPLICATIONS

This application is a continuation of U.S. patent application Ser. No. 17/108,110, filed Dec. 1, 2020, which is a continuation of U.S. patent application Ser. No. 16/782,866, filed Feb. 5, 2020, which claims priority to Patent Application No. GB1901559.3 filed in the United Kingdom on Feb. 5, 2019, the entire contents of each which are incorporated herein by reference.

The present invention relates to pyrazole derivatives of formula (B) and formula (C) as described herein, which are valuable intermediates in the production of agrochemicals and pharmaceuticals. The invention extends to the manufacture of such pyrazole derivatives, and their subsequent use in the manufacture of agrochemicals and/or pharmaceuticals.

In a first aspect there is provided a compound of formula (B)

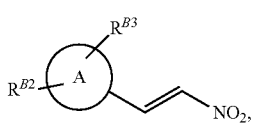

(B)

wherein ring A as is a di-substituted pyrazole, substituted a ring nitrogen by $R^{B2}$ and substituted on a ring carbon by $R^{B3}$, wherein $R^{B2}$ is $C_1$-$C_3$ alkyl or $C_1$-$C_3$fluoroalkyl and $R^{B3}$ is halogen, $C_1$-$C_3$fluoroalkyl, $C_1$-$C_3$haloalkoxy, $C_1$-$C_3$alkoxy, $C_1$-$C_3$haloalkyl, $C_1$-$C_3$fluoroalkyl, $C_1$-$C_3$haloalkoxy, $C_1$-$C_3$alkoxy, or $C_1$-$C_3$alkyl.

In a second aspect there is provided a compound of formula (C)

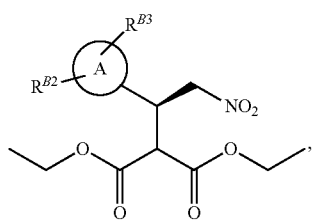

(C)

wherein ring A as is a di-substituted pyrazole, substituted on a ring nitrogen by $R^{B2}$ and substituted on a ring carbon by $R^{B3}$, wherein $R^{B2}$ is $C_1$-$C_3$ alkyl or $C_1$-$C_3$fluoroalkyl, and $R^{B3}$ is halogen, $C_1$-$C_3$fluoroalkyl, $C_1$-$C_3$haloalkoxy, $C_1$-$C_3$alkoxy, $C_1$-$C_3$haloalkyl, $C_1$-$C_3$fluoroalkyl, $C_1$-$C_3$haloalkoxy, $C_1$-$C_3$alkoxy, or $C_1$-$C_3$alkyl.

Compounds of formulae (B) and (C), may be used as intermediates in the manufacture of pharmaceuticals and agrochemicals comprising pyrazolo-pyrrolidone motifs. For example, US2007/0123508 describes 2-oxo-1-pyrrolidone derivatives for use as PAR2 inhibitors, compounds of formulae (B), (C), (D) and (E) may be used in the synthesis of such compounds wherein $R^1$ of the compound of US2007/0123508 is a substituted pyrazole. The manufacture of novel herbicidal compounds using compounds of formula formulae (B), and (C), is also described herein.

Compounds of formula (B) may be prepared from a halogenated pyrazole of formula (A)

(A)

wherein ring A, $R^{B2}$ and $R^{B3}$ are as defined above, and Hal is halogen selected from iodo, bromo and chloro, by reacting the compound of formula (A) with isopropylmagnesium chloride-lithium chloride in a suitable solvent, such as tetrahydrofuran, at −20° C. After two hours, 1-dimethylamino-2-nitroethylene is added and the reaction is slowly warmed to room temperature over the course of one hour. This affords the desired nitrovinyl pyrazole of formula (B) after work up and purification (Reaction scheme 1). Compounds of formula (A) are either known or can be prepared according to methods well known in the art.

Reaction scheme 1

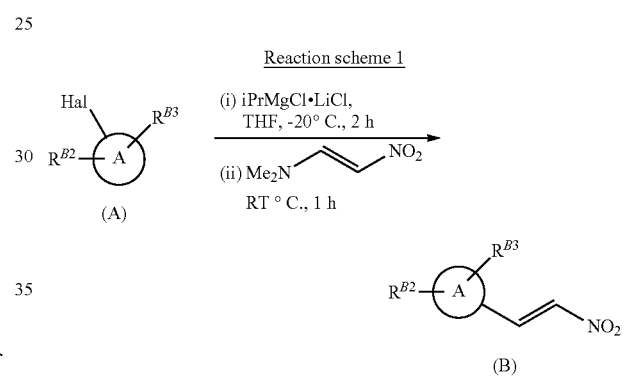

Nitrovinyl pyrazole compounds of formula (B) can also be prepared by reacting the corresponding pyrazole aldehyde (x) and nitromethane together, with a suitable base, in a suitable solvent followed by dehydration step, as shown in Reaction scheme 1.1 below. Such methods are reported in WO2016/100050 and WO2019/169153.

Reaction scheme 1.1

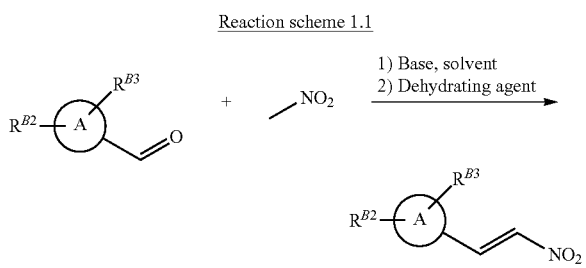

The nitrovinyl pyrazole compound of formula (B) is then reacted with a malonate, such as diethylmalonate, in a suitable solvent, such as toluene, under enantioselective nickel catalysis as described in *J. Am. Chem. Soc.* 2005, 127, 9958-9959, to afford the enantio-enriched malonate addition product that is the compound of formula (C) as shown in Reaction scheme 2.

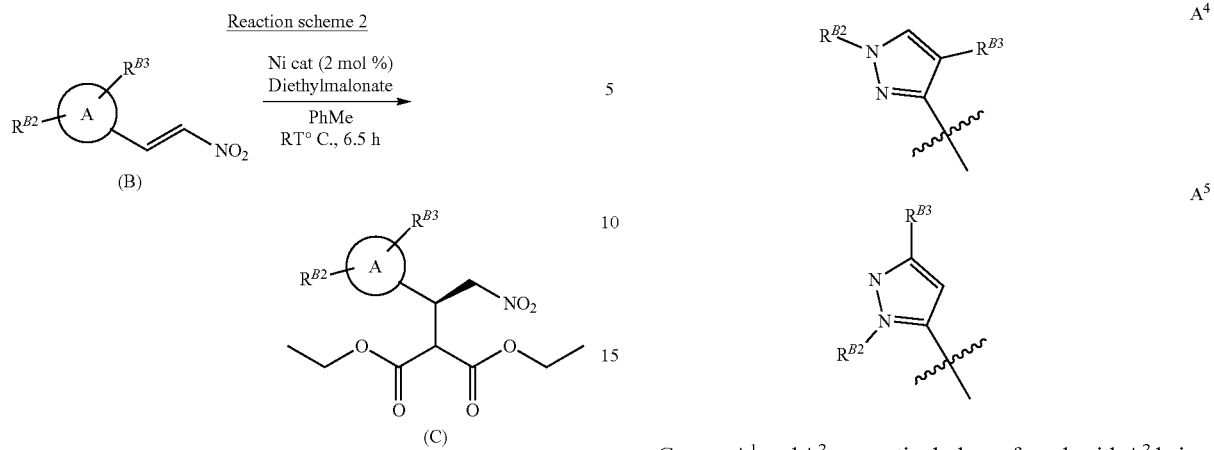

In compounds of formulae (A), (B), and (C), as described herein, ring A is a pyrazole moiety carrying two substituents, wherein one of said substituents ($R^{B2}$) is borne by a ring nitrogen, and a second substituent ($R^{B3}$) is borne on a ring carbon atom. Clearly with such a configuration, A is carbon linked to the rest of the respective molecule.

When A is di-substituted and $R^{B3}$ is borne on the ring carbon atom adjacent the substituted ring nitrogen atom said $R^{B3}$ substituent may be defined as $R^{B3SN}$. For the avoidance of doubt $R^{B3SN}$ is a sub-definition of $R^{B3}$ used purely to denote positional placement within the pyrazole moiety, and therefore $R^{B3SN}$ is also selected from the group consisting of halogen, $C_1$-$C_3$fluoroalkyl, $C_1$-$C_3$haloalkoxy, $C_1$-$C_3$alkoxy, and $C_1$-$C_3$alkyl. Thus, when A is di-substituted, it may be represented by groups $A^1$, $A^2$, $A^3$, $A^4$, or $A^5$, as shown below, wherein $R^{B2}$, $R^{B3}$ and $R^{B3SN}$ are as defined above and the jagged line denotes the point of attachment to the rest of the relevant molecule.

Groups $A^1$ and $A^2$ are particularly preferred, with $A^2$ being the most preferred of the di-substituted pyrazoles.

Preferably $R^{B2}$ is selected from the group consisting of methyl, ethyl, n-propyl, fluoromethyl, trifluoromethyl, fluoroethyl, difluoroethyl and trifluoroethyl. More preferably $R^{B2}$ is selected from the group consisting of methyl, ethyl, n-propyl, trifluoromethyl and difluoroethyl. More preferably still, $R^{B2}$ is selected from the group consisting of methyl, ethyl, and difluoroethyl.

Preferably $R^{B3}$ (and thus also $R^{B3SN}$) is selected from chloro, fluoro, bromo, methyl, ethyl, diluoromethyl, trifluoromethyl $C_1$-$C_3$haloalkoxy, $C_1$-$C_3$alkoxy, or $C_1$-$C_3$alkyl.

As used herein, the term "halogen" or "halo" refers to fluorine (fluoro), chlorine (chloro), bromine (bromo) or iodine (iodo), preferably fluorine, chlorine or bromine.

Each alkyl moiety either alone or as part of a larger group may be straight-chained or branched, and as used herein the term specifically also includes cyclopropyl. Typically, the alkyl is, for example, methyl, ethyl, n-propyl, cylcopropyl, and isopropyl.

Table 1 and 2 below provide specific examples of compounds of formulae (B) and (C) for use in the invention.

TABLE 1

Compounds of formula B according to the invention

| Cmpd. No. | Name | Structure |
|---|---|---|
| B.001 | (E)-N,N-dihydroxy-2-[1-methyl-5-(trifluoromethyl)pyrazol-3-yl]ethenamine | 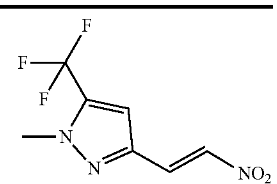 |
| B.002 | (E)-N,N-dihydroxy-2-[1-methyl-5-(trifluoromethyl)pyrazol-4-yl]ethenamine | 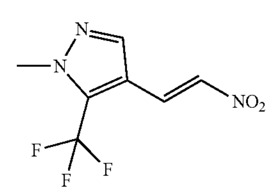 |
| B.003 | (E)-2-(5-chloro-1-methyl-pyrazol-3-yl)-N,N-dihydroxy-ethenamine | 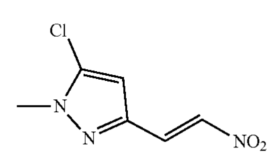 |

TABLE 1-continued

Compounds of formula B according to the invention

| Cmpd. No. | Name | Structure |
|---|---|---|
| B.004 | (E)-2-(5-chloro-1-methyl-pyrazol-4-yl)-N,N-dihydroxy-ethenamine | 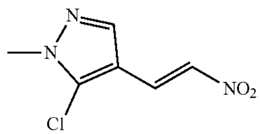 |
| B.005 | (E)-2-(5-fluoro-1-methyl-pyrazol-3-yl)-N,N-dihydroxy-ethenamine | 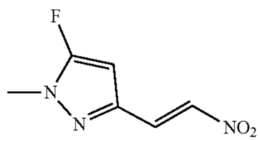 |
| B.006 | (E)-2-(5-fluoro-1-methyl-pyrazol-4-yl)-N,N-dihydroxy-ethenamine | 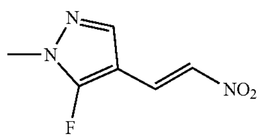 |

TABLE 2

Compounds of formula C according to the invention

| Cmpd. No. | Name | Structure |
|---|---|---|
| C.001 | diethyl 2-[(1R)-2-(dihydroxyamino)-1-[1-methyl-5-(trifluoromethyl)pyrazol-3-yl]ethyl]propanedioate | 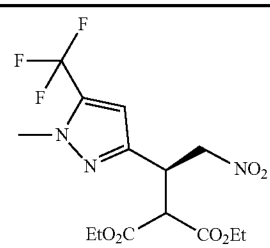 |
| C.002 | diethyl 2-[(1S)-2-(dihydroxyamino)-1-[1-methyl-5-(trifluoromethyl)pyrazol-4-yl]ethyl]propanedioate | 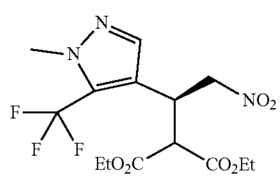 [SMILES: CCOC(=O)C(C(=O)OCC)[C@H](C[N+](=O)[O-])c1cnn(C)c1C(F)(F)F] |
| C.003 | diethyl 2-[(1R)-1-(5-chloro-1-methyl-pyrazol-3-yl)-2-(dihydroxyamino)ethyl]propanedioate | 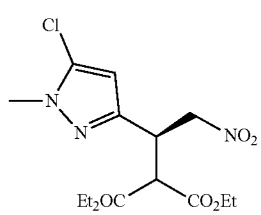 |
| C.004 | diethyl 2-[(1S)-1-(5-chloro-1-methyl-pyrazol-4-yl)-2-(dihydroxyamino)ethyl]propanedioate | 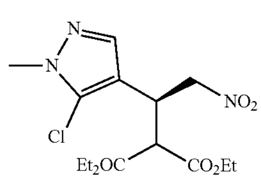 |

TABLE 2-continued

Compounds of formula C according to the invention

| Cmpd. No. | Name | Structure |
|---|---|---|
| C.005 | diethyl 2-[(1R)-2-(dihydroxyamino)-1-(5-fluoro-1-methyl-pyrazol-3-yl)ethyl]propanedioate | 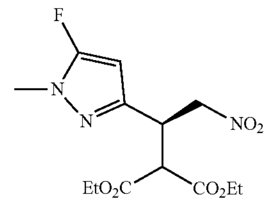 |
| C.006 | diethyl 2-[(1S)-2-(dihydroxyamino)-1-(5-fluoro-1-methyl-pyrazol-4-yl)ethyl]propanedioate | 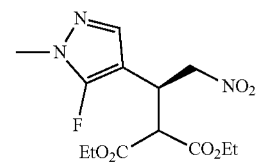 [SMILES: CCOC(=O)C(C(=O)OCC)[C@H](C[N+](=O)[O-])c1cnn(C)c1F] |

Compounds of formula (B) and (C) as described herein, may be used to synthesise pyrazolo-lactam-carboxylates of formula (D),

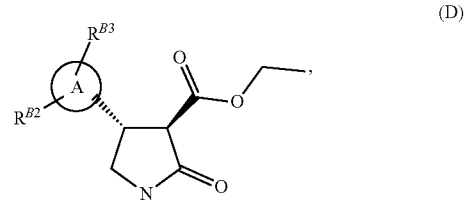

(D)

wherein ring A, $R^{B2}$ and $R^{B3}$ are as defined herein, and pyrazolo-lactam-carboxylic acid derivatives of formula (E),

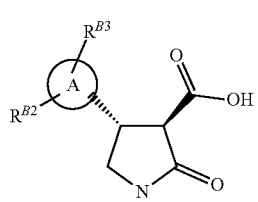

also wherein ring A, $R^{B2}$ and $R^{B3}$ are as defined herein. These novel compounds form yet further aspects of the invention.

The reductive cyclisation of the compound of formula (C), using a suitable reducing agent, such as sodium borohydride, with a suitable catalyst, such as nickel chloride, in a suitable solvent, such as ethanol, affords a pyrazolo-lactam-carboxylate of formula (D) (Reaction scheme 3 below).

Reaction scheme 3

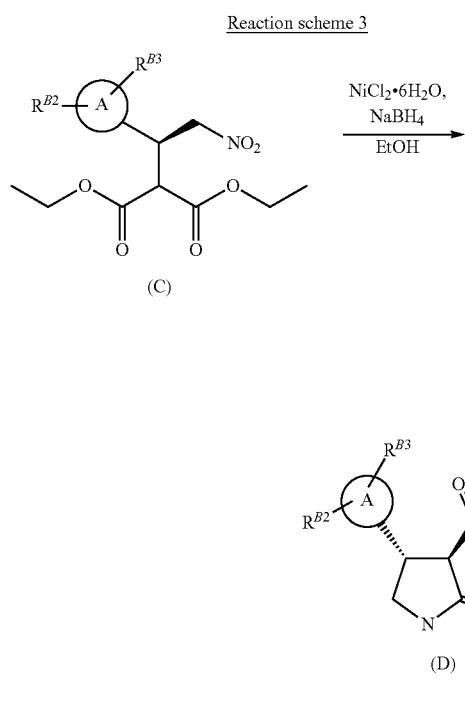

The compound of formula (D) may then be hydrolysed in an aqueous hydroxide/ethanol mixture to afford the appropriate pyrazolo-lactam-3-carboxylic acid derivative of formula (E), as shown in Reaction scheme 4.

Reaction scheme 4

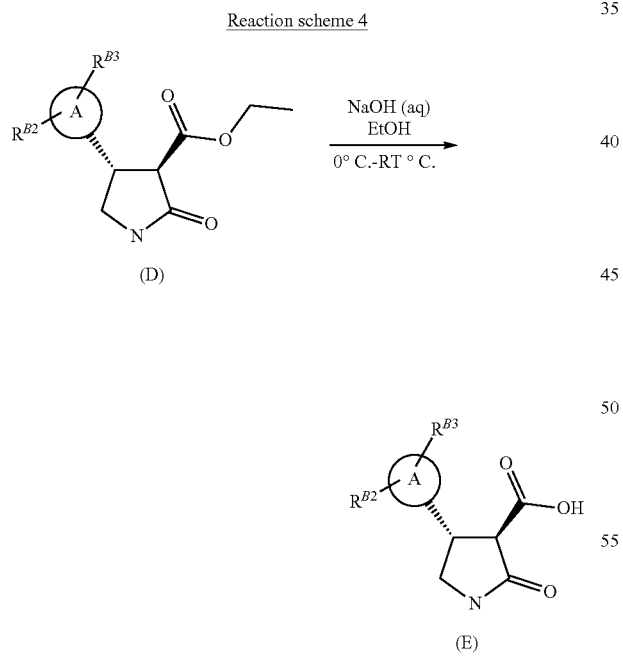

Compounds of formula (D) and formula (E) are also valuable intermediates in the production of pyrazolo-lactam herbicides, in particular as they give rise to the preferred herbicidal enantiomer. Tables 3 and 4 below provide specific examples of compounds of formulae (D) and (E) for use in the invention.

TABLE 3

Compounds of formula (D) according to the invention

| Cmpd. No. | Name | Structure |
|---|---|---|
| D.001 | ethyl (3R,4R)-4-[1-methyl-5-(trifluoromethyl)pyrazol-3-yl]-2-oxo-pyrrolidine-3-carboxylate | 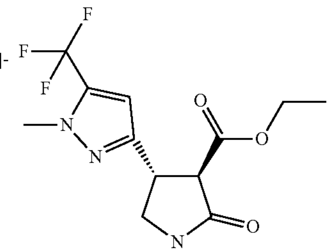 |
| D.002 | ethyl (3R,4S)-4-[1-methyl-5-(trifluoromethyl)pyrazol-4-yl]-2-oxo-pyrrolidine-3-carboxylate | 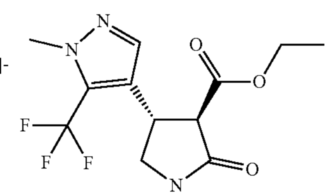 |
| D.003 | ethyl (3R,4R)-4-(5-chloro-1-methyl-pyrazol-3-yl)-2-oxo-pyrrolidine-3-carboxylate | 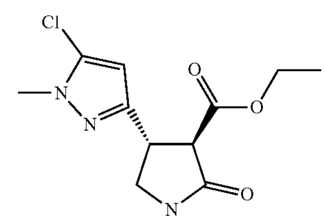 |
| D.004 | ethyl (3R,4S)-4-(5-chloro-1-methyl-pyrazol-4-yl)-2-oxo-pyrrolidine-3-carboxylate | 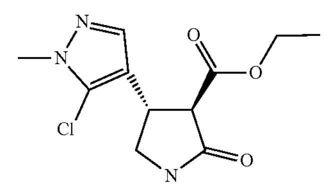 |
| D.005 | ethyl (3R)-4-(5-fluoro-1-methyl-pyrazol-3-yl)-2-oxo-pyrrolidine-3-carboxylate | 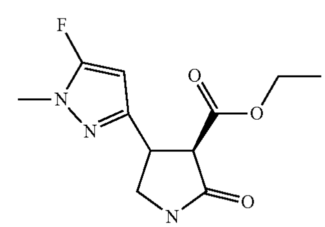 |
| D.006 | ethyl (3R)-4-(5-fluoro-1-methyl-pyrazol-4-yl)-2-oxo-pyrrolidine-3-carboxylate | 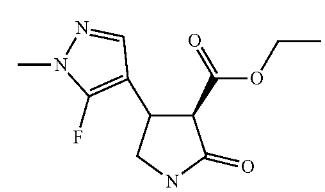 |

TABLE 4

Compounds of formula (E) according to the invention

| Cmpd. No. | Name | Structure |
|---|---|---|
| E.001 | (3R,4R)-4-[1-methyl-5-(trifluoromethyl)pyrazol-3-yl]-2-oxo-pyrrolidine-3-carboxylic acid | 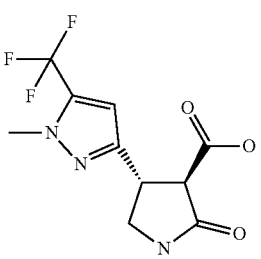 |
| E.002 | (3R,4S)-4-[1-methyl-5-(trifluoromethyl)pyrazol-4-yl]-2-oxo-pyrrolidine-3-carboxylic acid | 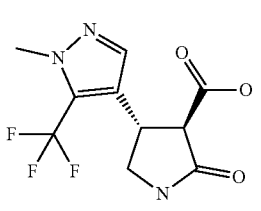 |
| E.003 | (3R,4S)-4-(5-chloro-1-methyl-pyrazol-4-yl)-2-oxo-pyrrolidine-3-carboxylic acid | 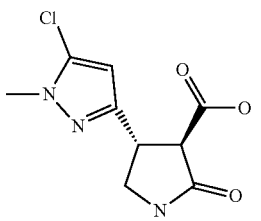 |
| E.004 | (3R,4S)-4-(5-chloro-1-methyl-pyrazol-4-yl)-2-oxo-pyrrolidine-3-carboxylic acid | 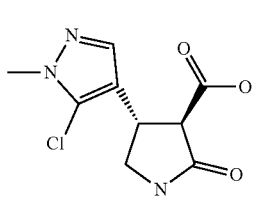 |
| E.005 | (3R,4R)-4-(5-fluoro-1-methyl-pyrazol-3-yl)-2-oxo-pyrrolidine-3-carboxylic acid | 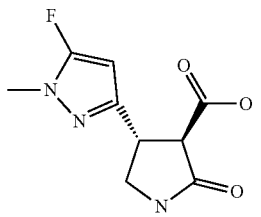 |
| E.006 | (3R,4S)-4-(5-fluoro-1-methyl-pyrazol-4-yl)-2-oxo-pyrrolidine-3-carboxylic acid | 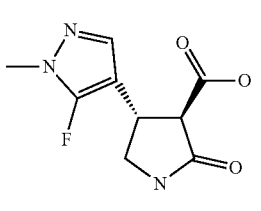 |

The process for the manufacture of novel pyrazolo-lactam herbicides of formula (G) from compounds of formula (E), is described below in general terms in Reaction schemes 5 and 6, and with respect to a specific herbicidal compounds in the Examples.

Reaction scheme 5

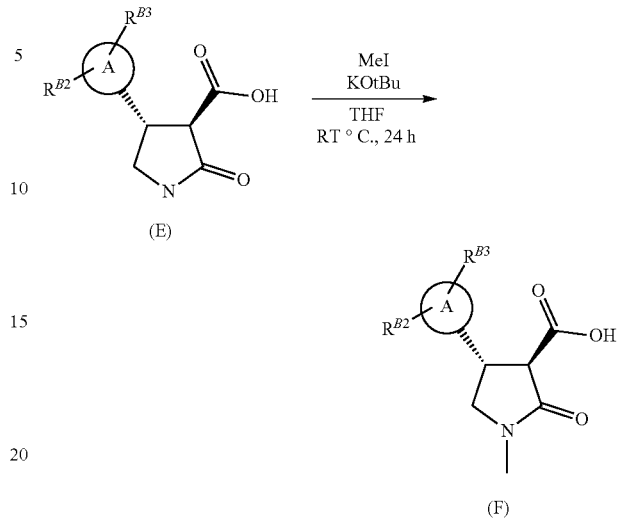

Compounds of formula (E) are methylated on the lactam nitrogen using excess base, such as potassium tertiary butoxide, with methyl iodide or alternative methylating reagents, in a suitable solvent, such as tetrahydrofuran (Reaction scheme 5 above).

The 3-carboxyl substituted N-methyl lactam of formula (F) is coupled with an aniline of formula $R^2$—$NH_2$ (wherein $R^2$ is as defined infra) to afford a herbicidal pyrazolo-lactam carboxamide of formula (G), using standard amide coupling conditions, such as propanephosphonic acid anhydride in a suitable solvent, such as dichloromethane, with a suitable base (Reaction scheme 6).

Reaction scheme 6

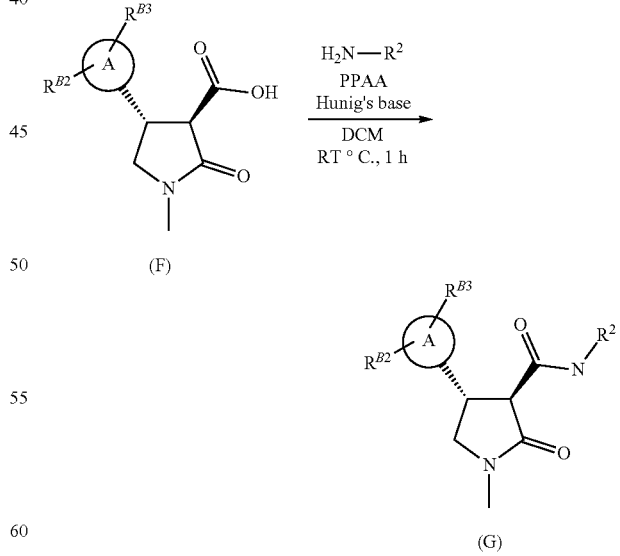

For anilines of formula $R^2$—$NH_2$ and herbicidal compounds of formula (G), $R^2$ substituents include hydrogen, $C_1$-$C_6$alkyl, —$C_r$alkoxy$C_s$alkyl, $C_1$-$C_6$haloalkyl, —$C_r$alkoxy$C_s$haloalkyl, $C_2$-$C_6$alkenyl, $C_2$-$C_6$alkynyl, and —$(CR^{21}R^{22})_rR^{20}$, wherein each $R^{20}$ is independently —C(O)OR$^{23}$, —OC(O)R$^{23}$, —C$_3$-C$_6$cycloalkyl, or an -aryl, -aryloxy, -heteroaryl, -heteroaryloxy or -heterocyclyl ring, wherein said ring is optionally substituted by 1 to 3 independent R$^{25}$; r is an integer of 1, 2, 3, 4, or 5, s is an integer of 1, 2, 3, 4, or 5, and the sum of r+s is less than or equal to 6; t is an integer of 0, 1, 2, 3, 4, 5 or 6, each R$^{21}$ is independently hydrogen or C$_1$-C$_2$ alkyl; each R$^{22}$ is independently hydrogen or C$_1$-C$_2$ alkyl; R$^{23}$ is hydrogen or C$_1$-C$_4$alkyl.

In certain embodiments, where R$^2$ is an aryl or heteroaryl ring optionally substituted by 1 to 3 R$^{25}$, and said aryl or heteroaryl ring is selected from the group consisting of a phenyl, pyridinyl, and a thienyl ring system, it may be represented by the following generic structure

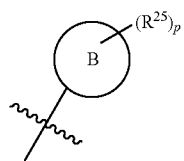

wherein ring B is a phenyl, pyridinyl, or thienyl ring, p is an integer or 0, 1, 2, or 3, and the jagged line represents the point of attachment of the ring to the rest of the molecule, in this case via the amide nitrogen.

In certain embodiments R$^2$ is selected from the group consisting of R$^2$-1, R$^2$-2, R$^2$-3, R$^2$-4, R$^2$-5, and R$^2$-6, wherein p and the jagged line are as described previously, and each R$^{25}$ is independently halogen, C$_1$-C$_6$alkyl, C$_1$-C$_6$haloalkyl, C$_1$-C$_6$alkoxy, C$_1$-C$_6$haloalkoxy, cyano, nitro, C$_1$-C$_6$alkylthio, C$_1$-C$_6$alkylsulphinyl, or C$_1$-C$_6$alkylsulphonyl More preferably each R$^{25}$ is independently halogen, C$_1$-C$_4$ alkyl, C$_1$-C$_3$ haloalkyl, C$_1$-C$_3$alkoxy, or C$_1$-C$_3$haloalkoxy; even more preferably chloro, fluoro, bromo, C$_1$-C$_2$haloalkyl, C$_1$-C$_2$haloalkoxy, or C$_1$-C$_2$alkoxy; more preferably still fluoro, ethyl, trifluoromethyl, difluoroethyl, methoxy, difluoromethoxy, or trifluoromethoxy. As stated herein, the value of p is 1, 2 or 3. Preferably p is 0, 1, or 2 and each R$^{25}$ is borne by a ring carbon atom.

Anilines of formula R$^2$—NH$_2$ are either known or can be prepared according to methods well known in the art.

Reaction schemes 1a, 2a, 3a, 4a, and 5a shown below exemplify the compounds and processes of the invention as described above for a preferred set of embodiments, wherein the pyrazole ring in the compound of formula (A) has the structure described as A2 supra. Unless otherwise stated, R$^{B2}$, R$^{B3}$, Hal, and R$^2$ are as defined hereinbefore.

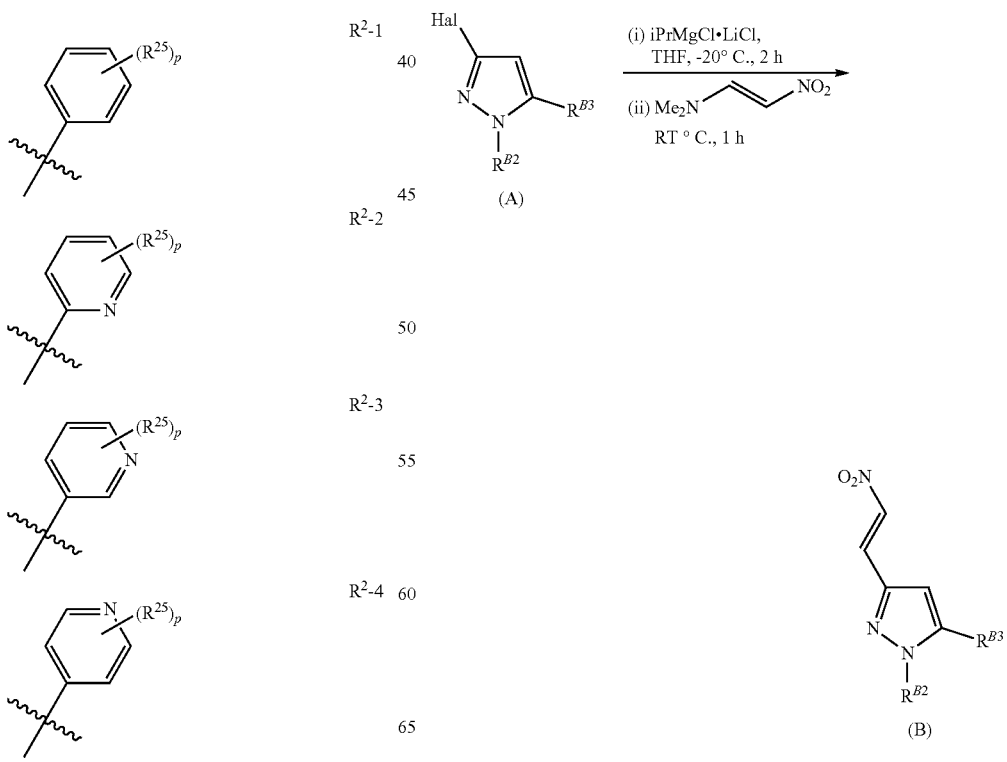

Reaction scheme 2a
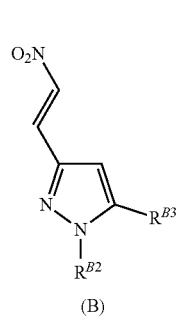
(B)
Ni Cat (2 mol %)
Diethylmalonate
———————————→
PhMe
RT °C., 6.5 h
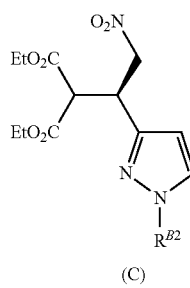
(C)
Reaction scheme 3a
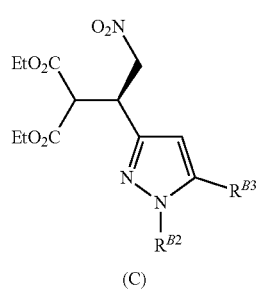
(C)
NiCl$_2$·6H$_2$O,
NaBH$_4$
————————→
EtOH
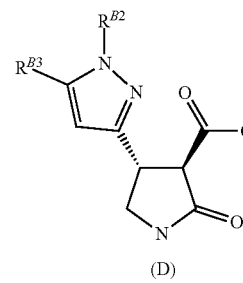
(D)
Reaction scheme 4a
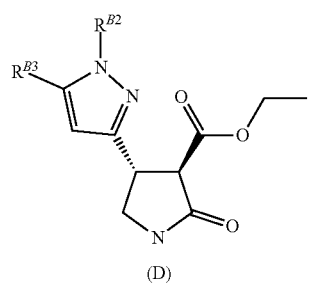
(D)
NaOH (aq) EtOH
————————→
0° C.-RT ° C.
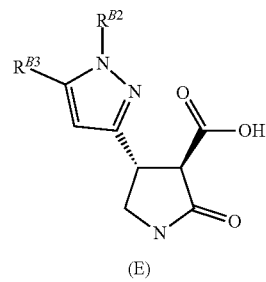
(E)
Reaction scheme 5a
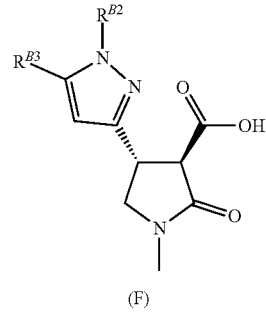
(E)
MeI
KOtBu
————→
THF
RT ° C., 24 h
(F)
Reaction scheme 6a
(F)
H$_2$N—R$^2$
PPAA
Hunig's base
————————→
DCM
RT ° C., 1 h

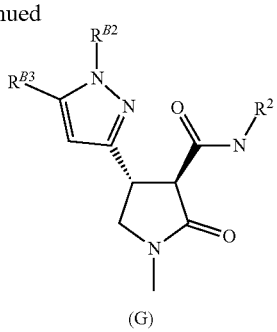

(G)

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Example 1: Preparation of the Herbicidal Compound (3S,4R)—N-(2,3-difluorophenyl)-1-methyl-4-[1-methyl-5-(trifluoromethyl)pyrazol-3-yl]-2-oxo-pyrrolidine-3-carboxamide water, was then added dropwise over 5 minutes, resulting in a colourless solution and the reaction was stirred at 0° C. for a further 20 minutes. Potassium iodide (75.7 mmol, 12.6 g), in 20 mL of water, was added dropwise to the reaction and the mixture was then stirred for a further 4 hours. The reaction was quenched with saturated sodium thiosulfate until the mixture became clear. The mixture was then diluted with dichloromethane and the phases were separated. The aqueous was further extracted with dichloromethane and the combined organic extracts were washed with water, dried (MgSO4), filtered and concentrated under vacuum to afford a pale yellow oil. The crude product was purified by column chromatography (EtOAc/hexanes gradient elution) to afford 3-iodo-1-methyl-5-(trifluoromethyl)pyrazole as a colourless oil, 3.9 g, (47%). $^1$H NMR (400 MHz, CDCl$_3$) δ=6.76 (s, 1H) 4.01 (d, J=0.61 Hz, 3H).

Step 2 1-Methyl-3-[(E)-2-nitrovinyl]-5-(trifluoromethyl)pyrazole

Isopropylmagnesium chloride-Lithium chloride in THF (23.55 mmol, 1.3 mol/L) was added dropwise to 3-iodo-1-methyl-5-(trifluoromethyl)pyrazole (5.0 g, 18.12 mmol) in THF (90 mL) at −20° C. and the mixture was stirred for 2 hours. 1-Dimethylamino-2-nitroethylene (27.17 mmol, 3.321 g) was added and the reaction was slowly warmed to RT over 1 hour. The reaction mixture was then carefully quenched with 2 M HCl, and extracted with ethyl acetate. The organic extracts were washed with brine, dried (MgSO4), filtered, concentrated and purified by chromatog-

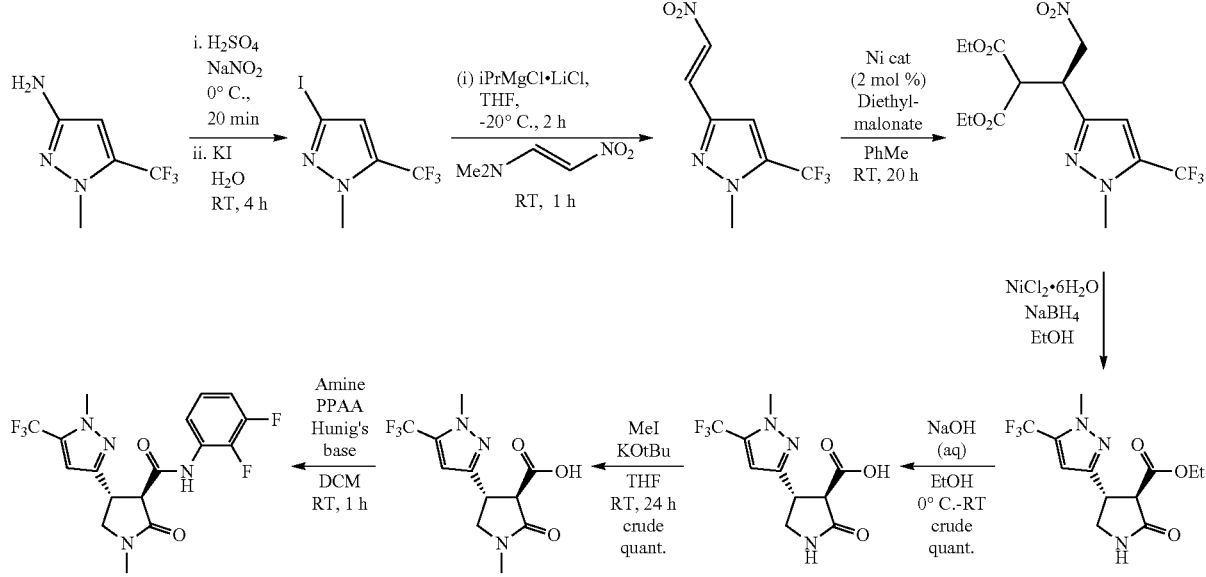

The Nickel catalyst used in step 3, which catalyses the asymmetric malonate addition to the nitro olefin, can be prepared as in *J. Am. Chem. Soc.* 2005, 127, 9958-9959.

Step 1 3-iodo-1-methyl-5-(trifluoromethyl)pyrazole

The compound 1-methyl-5-(trifluoromethyl)pyrazol-3-amine (5.00 g, 30.3 mmol) was stirred in 9M sulfuric acid (818 mmol, 91 mL) in a 500 mL beaker, using an overhead stirrer at 0° C. (ice bath) until a homogenous mixture resulted. Sodium nitrite (60.6 mmol, 4.18 g), in 10 mL of raphy (EtOAc/cyclohexane gradient elution) to afford 1-methyl-3-[(E)-2-nitrovinyl]-5-(trifluoromethyl)pyrazole (74.6%) as a yellow oil, 2.99 g (74.6%).

$^1$H NMR (400 MHz, CDCl$_3$) δ=7.89 (d, J=13.7 Hz, 1H), 7.63 (d, J=13.7 Hz, 1H), 6.88 (s, 1H), 4.05 (d, J=0.6 Hz, 3H).

Step 3 Diethyl 2-[(1S)-1-[1-methyl-5-(trifluoromethyl)pyrazol-3-yl]-2-nitro-ethyl]propanedioate To a solution of 1-methyl-3-[(E)-2-nitrovinyl]-5-(trifluoromethyl)pyrazole (0.650 g, 2.94 mmol) in toluene (19.5 mL) was added diethyl malonate (0.676 mL, 4.41 mmol) followed by Nickel(II)Bis[(1R,2R)—N1,N2-bis(phenylmethyl)-1,2-cyclohexanediamine-N1,N2]dibromide (0.0588 mmol, 0.0472 g), and the mixture was stirred at ambient temperature for 20 hours.

The reaction mixture was washed with water (2×10 mL) and the organic phase separated, concentrated and purified by chromatography (EtOAc/cyclohexane gradient elution) to afford diethyl 2-[(1 S)-1-[1-methyl-5-(trifluoromethyl)pyrazol-3-yl]-2-nitro-ethyl]propanedioate as pale yellow oil, 1.07 g (95%).

$^1$H NMR (400 MHz, CDCl$_3$) δ=6.53 (s, 1H), 5.01 (dd, 1H), 4.88 (dd, J=4.3, 13.9 Hz, 1H), 4.35 (ddd, J=4.4, 7.7, 9.0 Hz, 1H), 4.22 (q, 2H), 4.16 (q, J=7.1 Hz, 2H), 3.90 (s, 3H), 3.89 (d, 1H), 1.26 (t, 3H), 1.20 (t, J=7.2 Hz, 3H).

Step 4 Ethyl (3R,4R)-4-[1-methyl-5-(trifluoromethyl)pyrazol-3-yl]-2-oxo-pyrrolidine-3-carboxylate To a solution of diethyl 2-[(1R)-1-[1-methyl-5-(trifluoromethyl)pyrazol-3-yl]-2-nitro-ethyl]propanedioate (1.07 g, 2.81 mmol) in ethanol (42.1 mL) cooled to 0-5° C. (ice bath) under nitrogen, was added dichloronickel hexahydrate (2.95 mmol, 0.700 g). Sodium borohydride (8.42 mmol, 0.325 g) was then added portionwise to the pale greenish-blue solution. After 30 minutes the cooling was removed and the reaction mixture allowed to warm to ambient temperature. After stirring for 5 hours, at ambient temperature, the reaction mixture was cooled to 5-10° C., in an ice-water bath, and slowly quenched with ammonium chloride solution, and the mixture stirred for a further 20 minutes. The mixture was then diluted with EtOAc (20 mL), and filtered through a bed of celite, washing through with portions of water and EtOAc. The collected two-phase mixture was concentrated to remove the bulk of solvent and the residue transferred to a separating funnel, diluted with EtOAc (20 mL) and the organic phase separated. The aqueous phase was further extracted with EtOAc (2×25 mL) and all organic extracts combined, passed through a phase separation concentrated and purified by chromatography (EtOAc/hexanes gradient elution) to afford a pale yellow oil, 0.61 g (77%) which crystallised on standing.

1H NMR (400 MHz, CDCl$_3$) δ=6.91 (br s, 1H), 6.47 (s, 1H), 4.28 (q, J=7.2 Hz, 2H), 4.14 (q, 1H), 3.94 (d, 3H), 3.80 (dt, J=1.0, 9.0 Hz, 1H), 3.63 (d, J=9.3 Hz, 1H), 3.52 (dd, J=8.2, 9.5 Hz, 1H), 1.32 (t, J=7.2 Hz, 3H).

Step 5 (3R,4R)-4-[1-methyl-5-(trifluoromethyl)pyrazol-3-yl]-2-oxo-pyrrolidine-3-carboxylic acid To a solution of ethyl (3R,4R)-4-[1-methyl-5-(trifluoromethyl)pyrazol-3-yl]-2-oxo-pyrrolidine-3-carboxylate (0.61 g, 2.0 mmol) in ethanol (6.0 mL) and water (2.0 mL) at 0° C. (ice bath) was added 2M sodium hydroxide (3 mL, 6.0 mmol). The reaction mixture was stirred at 0° C. for 30 minutes and then diluted with water (15 mL) and extracted with EtOAc (25 mL). The organic extracts were washed with water (10 mL), and the aqueous extracts combined and acidified to pH 2 with dilute HCl. The acidified aqueous extracts were then re-extracted with EtOAc (3×20 mL) and these organic extracts were run through a phase separation cartridge and concentrated affording a pale yellow oil, 0.54 g (quantitative) which crystallised on standing.

$^1$H NMR (400 MHz, CDCl3) δ=6.59 (s, 1H), 4.09 (q, 1H), 3.94 (s, 3H), 3.85-3.77 (m, 1H), 3.72 (d, J=10.0 Hz, 1H), 3.66-3.58 (m, 1H).

Step 6 (3R,4R)-1-methyl-4-[1-methyl-5-(trifluoromethyl)pyrazol-3-yl]-2-oxo-pyrrolidine-3-carboxylic acid To a stirred solution of (3R,4R)-4-[1-methyl-5-(trifluoromethyl)pyrazol-3-yl]-2-oxo-pyrrolidine-3-carboxylic acid (0.57 g, 2.1 mmol, 0.57 g) in tetrahydrofuran (16 mL), at room temperature, under a nitrogen atmosphere was added potassium tertiary butoxide (1.0M in THF) (4.5 mL, 4.5 mmol) giving a pale yellow fine suspension. To this suspension was added iodomethane (0.19 mL, 3.1 mmol), and stirring at room temp was continued for 20 h. The stirred reaction mixture was acidified to pH2 with dilute HCl and the mixture was diluted with water (10 mL) and extracted with EtOAc (3×30 mL). The combined organic extracts were washed with brine (15 mL), dried over magnesium sulfate, filtered and the filtrate concentrated giving a transparent amber gum, 0.63 g ((quantitative).

$^1$H NMR: (400 MHz, CDCl3) δ=6.68 (s, 1H), 3.97 (q, 1H), 3.94 (s, 3H), 3.76-3.68 (m, 3H), 2.99 (s, 3H).

Step 7 (3S,4R)—N-(2,3-difluorophenyl)-1-methyl-4-[1-methyl-5-(trifluoromethyl)pyrazol-3-yl]-2-oxo-pyrrolidine-3-carboxamide To a solution of (3R,4R)-1-methyl-4-[1-methyl-5-(trifluoromethyl)pyrazol-3-yl]-2-oxo-pyrrolidine-3-carboxylic acid (0.61 g, 2.1 mmol) in dichloromethane (15 mL) was added 2,3-difluoroaniline (0.21 mL, 2.1 mmol). Propylphosphonic anhydride (50 mass %) in ethyl acetate (2.3 g, 3.6 mmol, 2.1 mL) was then added, and the reaction mixture was then immersed in a room temp water bath. N,N-Diisopropylethylamine (1.1 mL, 6.3 mmol) was added drop-wise, and the reaction was stirred at room temperature for 2.5 hour. The reaction mixture was quenched by the addition of water (15 mL) and transferred to a phase sep cartridge. The aqueous was further extracted with DCM (2×10 mL) and the combined organic extracts were concentrated and purified by chromatography (EtOAc/hexanes gradient elution) to afford a pink oil. Trituration with iso-hexane afforded a pale pink solid 398 mg (47%).

1H NMR: (400 MHz, CDCl$_3$) δ=10.16 (br s, 1H), 8.08-8.01 (m, 1H), 7.02 (ddt, J=2.1, 5.9, 8.3 Hz, 1H), 6.93-6.84 (m, 1H), 6.69 (s, 1H), 4.09 (q, 1H), 3.94 (s, 3H), 3.78 (d, J=9.5 Hz, 1H), 3.76-3.65 (m, 2H), 2.98 (s, 3H).

Chiral HPLC analysis, by the methods stated above, confirmed an enantiomeric ratio of 97:3.

Example 2 Preparation of (3S,4S)—N-(2,3-Difluorophenyl)-1-methyl-4-[1-methyl-5-(trifluoromethyl)pyrazol-4-yl]-2-oxo-pyrrolidine-3-carboxamide The herbicidal compound (3S,4S)—N-(2,3-Difluorophenyl)-1-methyl-4-[1-methyl-5-(trifluoromethyl)pyrazol-4-yl]-2-oxo-pyrrolidine-3-carboxamide was made in a directly analogous manner to that described above for (3S,4R)—N-(2,3-difluorophenyl)-1-methyl-4-[1-methyl-5-(trifluoromethyl)pyrazol-3-yl]-2-oxo-pyrrolidine-3-carboxamide in Example 1 above. NMR data for the single enantiomer is as follows:

1HNMR (CDCl$_3$) δ=10.05 (br s, 1H), 8.04-7.97 (m, 1H), 7.46 (s, 1H), 7.01 (ddt, J=2.1, 5.9, 8.3 Hz, 1H), 6.93-6.84 (m, 1H), 4.21 (q, J=8.8 Hz, 1H), 4.00 (s, 3H), 3.75 (t, J=9.5 Hz, 1H), 3.64 (d, J=9.4 Hz, 1H), 3.27 (dd, J=8.1, 9.9 Hz, 1H), 2.97 (s, 3H).

The invention claimed is:

1. A process for the manufacture of a compound of formula (G)

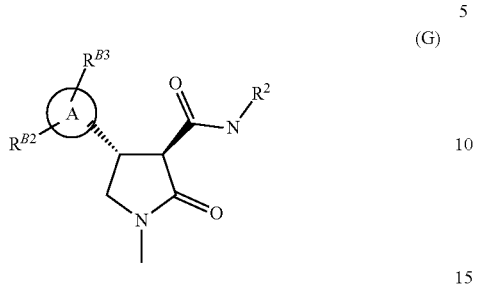

(G)

wherein ring A is a di-substituted pyrazole, substituted on a ring nitrogen by $R^{B2}$ and substituted on a ring carbon by $R^{B3}$;
$R^{B2}$ is $C_1$-$C_3$ alkyl or $C_1$-$C_3$fluoroalkyl,
$R^{B3}$ is halogen, $C_1$-$C_3$fluoroalkyl, $C_1$-$C_3$haloalkoxy, $C_1$-$C_3$alkoxy, $C_1$-$C_3$haloalkyl, or $C_1$-$C_3$alkyl;
$R^2$ is an aryl or heteroaryl ring optionally substituted by 1 to 3 $R_{25}$; and
each $R^{25}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl; said process comprising:

(i) reacting a compound of formula (A)

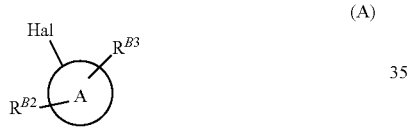

(A)

wherein ring A, $R^{B2}$ and $R^{B3}$ are as defined previously, and Hal is iodo, bronco or chloro, with 1-dimethyl-amino-2-nitroethylene to form a compound of formula (B)

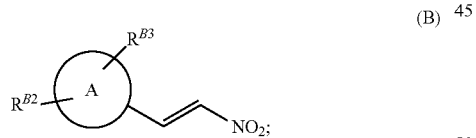

(B)

(ii) reacting the compound of formula (B) from step (i) with a malonate in solvent, under enantioselective nickel catalysis to give a compound of formula (C)

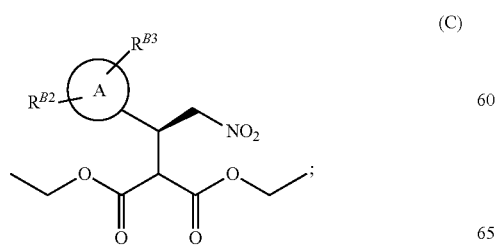

(C)

(iii) reacting the compound of formula (C) from step (ii) with a reducing agent in the presence of a catalyst to give a compound of formula (D)

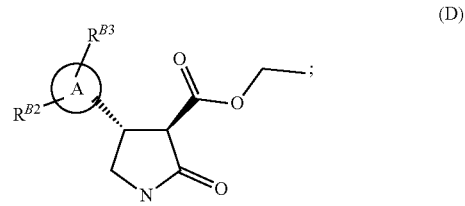

(D)

(iv) hydrolysing the compound of formula (D) from step (iii) in an aqueous hydroxide/ethanol mixture to give the compound of formula (E)

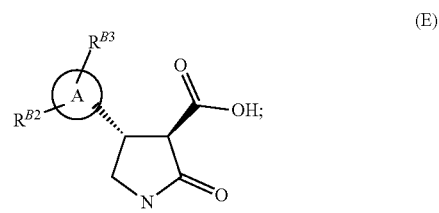

(E)

(v) methylating the lactam nitrogen of the compound of formula (E) formed in step (iv) using excess base in solvent, to form a compound of formula (1')

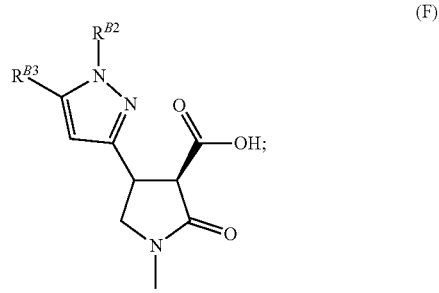

(F)

(vi) coupling the compound of formula (F) from step (v) with an aniline of formula $R_2$—$NH_2$ wherein $R^2$ is as defined above under standard amide coupling conditions, to yield a compound of formula (G)

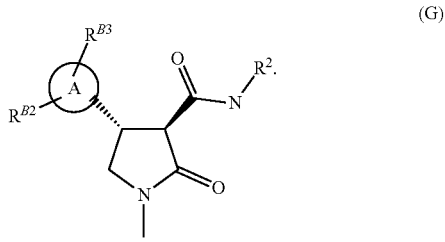

(G)

2. The process of claim 1, wherein ring A is A1, A2, A3, A4 or A5,

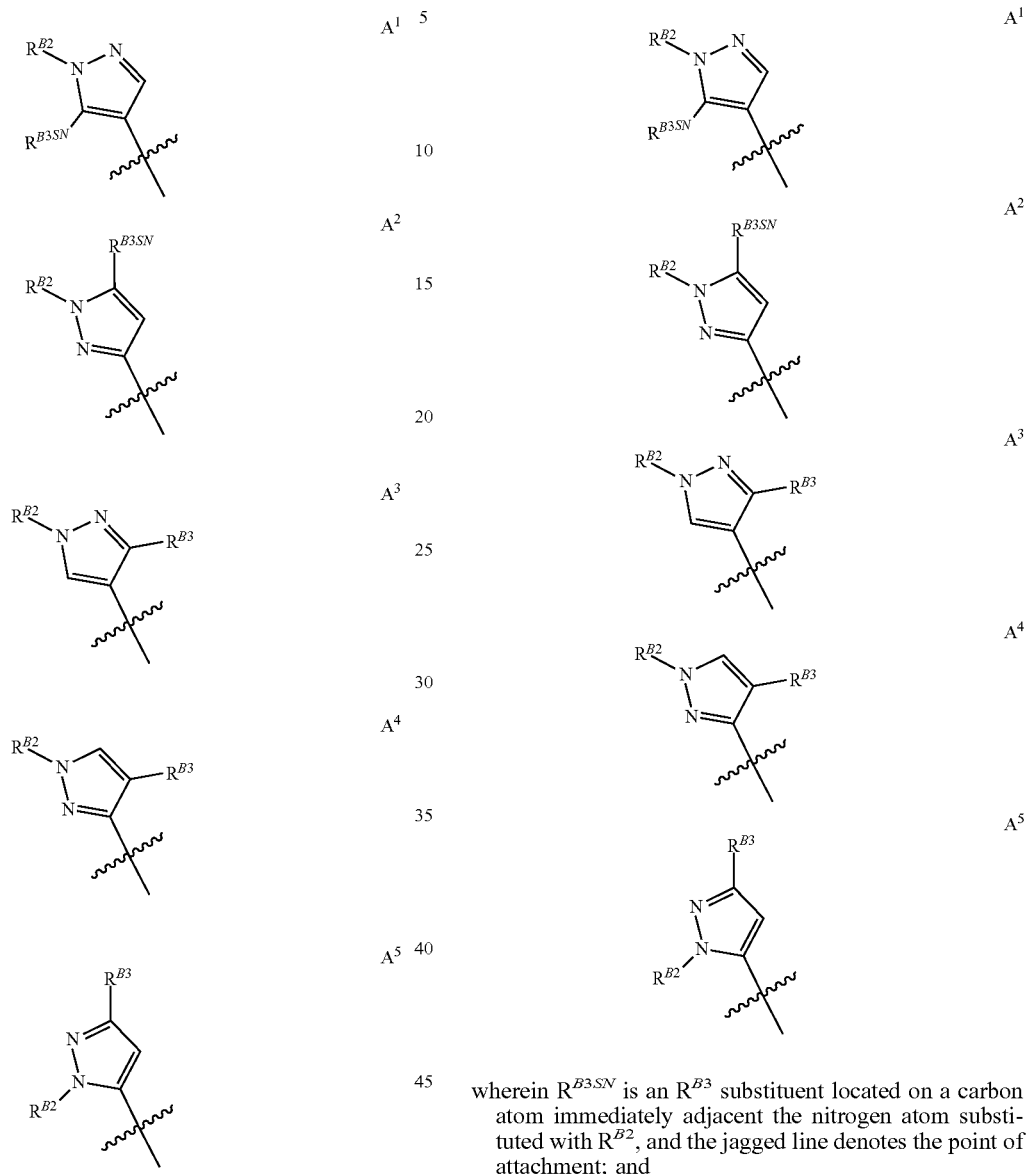

wherein $R^{B3.SN}$ is an $R^{B3}$ substituent located on a carbon atom immediately adjacent the nitrogen atom substituted with $R^{B2}$, and the jagged line denotes the point of attachment.

3. The process of claim 1, wherein $R^{B2}$ is selected from the group consisting of methyl, ethyl, n-propyl, fluoromethyl, trifluoromethyl, fluoroethyl, difluoroethyl and trifluoroethyl.

4. The process of claim 1, wherein $R^{B3}$ is selected from the group consisting of chloro, fluoro, bromo, methyl, ethyl, diluoromethyl, trifluoromethyl $C_1$-$C_3$haloalkoxy, $C_1$-$C_3$alkoxy, and $C_1$-$C_3$alkyl.

5. The process of claim 1 wherein Hal is iodo.

6. The process of claim 1, wherein Hal is bromo.

7. The process of claim 1, wherein Hal is chloro.

8. The process of claim 1, wherein ring A is A1, A2, A3, A4 or A5, wherein $R^{B3.SN}$ is an $R^{B3}$ substituent located on a carbon atom immediately adjacent the nitrogen atom substituted with $R^{B2}$, and the jagged line denotes the point of attachment; and wherein $R^{B2}$ is selected from the group consisting of methyl, ethyl, n-propyl, fluoromethyl, trifluoromethyl, fluoroethyl, difluoroethyl and trifluoroethyl.

9. The process of claim 8, wherein $R^{B3.SN}$ is selected from the group consisting of chloro, fluoro, bromo, methyl, ethyl, diluoromethyl, trifluoromethyl $C_1$-$C_3$haloalkoxy, $C_1$-$C_3$alkoxy, and $C_1$-$C_3$alkyl.

10. The process of claim 1, wherein ring A is A1, A2, A3, A4 or A5,

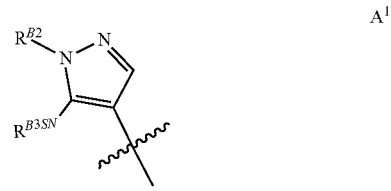

-continued

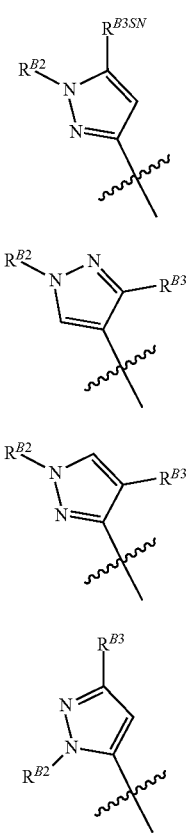

A²

A³

A⁴

A⁵ wherein $R^{B3SN}$ is an $R^{B3}$ substituent located on a carbon atom immediately adjacent the nitrogen atom substituted with $R^{B2}$, and the jagged line denotes the point of attachment; and wherein RB3SN is selected from the group consisting of chloro, fluoro, bromo, methyl, ethyl, diluoromethyl, trifluoromethyl $C_1$-$C_3$haloalkoxy, $C_1$-$C_3$alkoxy, and $C_1$-$C_3$alkyl.

11. The process of claim 1, wherein $R^{B2}$ is selected from the group consisting of methyl, ethyl, n-propyl, fluoromethyl, trifluoromethyl, fluoroethyl, difluoroethyl and trifluoroethyl; and $R^{B3}$ is selected from the group consisting of chloro, fluoro, bromo, methyl, ethyl, diluoromethyl, trifluoromethyl $C_1$-$C_3$haloalkoxy, $C_1$-$C_3$alkoxy, and $C_1$-$C_3$alkyl.

12. The process of claim 1, wherein $R^{B3}$ is selected from the group consisting of fluoro, chloro and trifluoromethyl.

13. The process of claim 12, wherein $R^{B2}$ is methyl.

14. The process of claim 1, wherein
 $R^2$ is selected from the group consisting of hydrogen, $C_1$-$C_6$alkyl, —$C_r$alkoxy$C_s$alkyl, $C_1$-$C_6$haloalkyl, —$C_r$alkoxy$C_s$haloalkyl, $C_2$-$C_6$alkenyl, $C_2$-$C_6$alkynyl, and —$(CR^{21}R^{22})_tR^{20}$; wherein
 r is an integer of 1, 2, 3, 4, or 5, s is an integer of 1, 2, 3, 4, or 5, and the sum of r+s is less than or equal to 6;
 each $R^{20}$ is independently —C(O)OR²³, —OC(O)R²³, —$C_3$-$C_6$cycloalkyl, or a ring system selected from an -aryl, -aryloxy, -heteroaryl, -heteroaryloxy and -heterocyclyl ring system, and said ring system is optionally substituted by 1 to 3 independent $R^{25}$;
 each $R^{21}$ is independently hydrogen or $C_1$-$C_2$ alkyl;
 each $R^{22}$ is independently hydrogen or $C_1$-$C_2$ alkyl;
 t is an integer of 0,1, 2, 3, 4, 5 or 6;
 and
 $R^{23}$ is hydrogen or $C_1$-$C_4$alkyl.

15. The process of claim 14, wherein R2 is an aryl or heteroaryl ring system optionally substituted by 1 to 3 $R^{25}$.

16. The process of claim 15, wherein the aryl or heteroaryl ring system is selected from a phenyl, pyridinyl or thienyl ring system.

17. The process of claim 15, wherein each $R^{25}$ is independently halogen, $C_1$-$C_4$ alkyl, $C_1$-$C_3$ haloalkyl, $C_1$-$C_3$alkoxy, or $C_1$-$C_3$haloalkoxy.

18. The process of claim 1 wherein each $R^{25}$ is independently halogen, $C_1$-$C_4$ alkyl, $C_1$-$C_3$ haloalkyl, $C_1$-$C_3$alkoxy, or $C_1$-$C_3$haloalkoxyl.

19. The process of claim 14, wherein $R^2$ is a phenyl, pyridinyl or thienyl ring system, substituted by 1 or 2 $R^{25}$, wherein each $R^{25}$ is borne on a ring carbon atom and is independently selected from the group consisting of fluoro, ethyl, trifluoromethyl, difluoroethyl, methoxy, difluoromethoxy, and trifluoromethoxy.

20. The process of claim 15, wherein each $R^{25}$ is independently chloro, fluoro, bromo, $C_1$-$C_2$haloalkyl, $C_1$-$C_2$haloalkoxy, or $C_1$-$C_2$alkoxy.

21. The process of claim 1 wherein each $R^{25}$ is independently chloro, fluoro, bromo, $C_1$-$C_2$haloalkyl, $C_1$-$C_2$haloalkoxy, or $C_1$-$C_2$alkoxy.

* * * * *